United States Patent [19]

Matsuo et al.

[11] Patent Number: 5,354,900
[45] Date of Patent: Oct. 11, 1994

[54] AN H-ANP PEPTIDE, PHARMACEUTICAL COMPOSITION AND METHOD OF USE

[75] Inventors: Hisayuki Matsuo, 6653, Ooaza-kihara, Kiyotake-cho, Miyazaki-gun, Miyazaki-ken; Kenji Kangawa, Miyazaki, both of Japan

[73] Assignees: Suntory Limited, Osaka; Hisayuki Matsuo, Miyazaki, both of Japan

[21] Appl. No.: 685,151

[22] Filed: Dec. 21, 1984

[30] Foreign Application Priority Data

Dec. 26, 1983 [JP] Japan ................. 58-243675

[51] Int. Cl.$^5$ .................. A61K 37/02; C07K 7/10
[52] U.S. Cl. ......................... 514/12; 514/13; 530/324; 530/325
[58] Field of Search .......... 260/112.5 R; 514/11.12, 514/13; 530/324, 325

[56] References Cited

U.S. PATENT DOCUMENTS 4,496,544  1/1985  Needleman ................. 514/13
4,508,712  4/1985  Needleman ................. 514/11

OTHER PUBLICATIONS

Life Sci. vol. 33, 297–302 (1983).
Biochem. & Biophys Res. Commun. 118, 131–139 (1984).
Science (1983) 71–73 vol. 221.
Biochem. & Biophys. Res. Commun. 122 (1984) 1076–1082.
Proc. of the Soc. Exper. Biol. Med. 170, 133–138 (1982).
Biochem. & Biophys. Res. Commun. (1983) 859–865 vol. 117, No. 3.
Can. Journal of Phys. & Pharm. 61, No. 2 (1983) 127–130.
Can. Journal of Phys. & Pharm. 60, No. 3, (1982) 324–330.
Life Sci. vol. 28, 89–94 (1980).
Jamieson, J. D. and Palade, G. E., "Specific Granules in Atrial Muscle Cells", *The Journal of Cell Biology*, vol. 23 (1964), pp. 151–172.
de Bold, A. J. et al, "A Rapid and Potent Natriuretic Response to Intravenous Injection of Atrial Myocardial Extract in Rats", *Life Sciences*, vol. 28 (1981), pp. 89–94.
Keeler, R., "Atrial Naturiuretic Factor has a Direct, Prostaglandin–independent Action on Kidneys", *Can. J. Physiol. Pharmacol.*, vol. 60 (1982) pp. 1078–1082.
Currie, M. G. et al, "Bioactive Cardiac Substances: Potent Vasorelaxant Activity in Mammalian Atria", *Science*, vol. 221 (1983), pp. 71–73.

*Primary Examiner*—Lester L. Lee
*Attorney, Agent, or Firm*—Burns, Doane, Swecker & Mathis

[57] ABSTRACT

There are disclosed a new peptide α-hANP of the following structure:

$$\begin{array}{c}
\phantom{xxxxxxxxxx}5\phantom{xxxxxxxxxxxxx}10\\
H-Ser-Leu-Arg-Arg-Ser-Ser-Cys-Phe-Gly-Gly-\\
-Arg-Met-\\
-Asp-Arg-①\\
-S-S-\\
\phantom{xx}15\phantom{xxxxxxxxxx}20\\
②-Ile-Gly-Ala-Gln-Ser-Gly-Leu-Gly-Cys-\\
25\\
-Asn-Ser-Phe-Arg-Tyr-OH
\end{array}$$

and acid addition salt thereof; a diuretic composition and a hypotensor composition containing the α-hANP or an acid addition salt thereof; and processes for the production thereof.

12 Claims, 4 Drawing Sheets

AN H-ANP PEPTIDE, PHARMACEUTICAL COMPOSITION AND METHOD OF USE

BACKGROUND OF THE INVENTION

1. Field of the Invention

The present invention relates to a novel peptide, a process for the production thereof, and a pharmaceutical composition containing the novel peptide as a diuretic or hypotensor.

2. Description of the Related Art

A normal regulation of the blood pressure in a human body is important for the maintenance of personal health, and various physical and humoral factors contribute to this regulation of the blood pressure. The physical factors include, for example, output, and the elasticity of the walls of blood vessels, etc. The humoral factors include, for example, the renin-angiotensin-aldosterone system, catecholamines, prostaglandins, kinin-kallikrein system, and natriuretic hormones including ouabain-like substances. Herein the term "natriuretic" will denote selective excretion of sodium cation relating to potassium cation.

Granules morphologically similar to granules present in peptide hormone-producing cells are found in human atrium (J. D. Jamieson and G. E. Palade, *J. Cell Biol.*, 23, 151, 1964). A homogenate of rat atrium and granules contained therein are known to show natriuretic action in rats (A. J. DeBold et. al., *Life Science*, 28, 89, 1981; R. Keeller, *Can. J. Physiol. Pharmacol.*, 60, 1078, 1982). Recently, Mark G., Currie S. et. al. suggested peptide-like substances with a molecular weight of 20,000 to 30,000, or not more than 10,000, present in atrium of humans, rabbits, swine, and rats, and having natriuretic action (*Science*, 221, 71–73, 1983).

SUMMARY OF THE INVENTION

The present invention provides a now peptide having natriuretic action and hypotensive of antihypertensive action. The peptide according to the present invention is hereinafter referred to as "α-human atrial natriuretic polypeptide" and abbreviated as "α-hANP".

There are also provided a process for the production of the peptide by chemical synthesis and a process for production of the peptide by the extraction of human atrium.

Another object of the present invention is to provide a pharmaceutical composition containing the peptide as a diuretic or hypotensor.

Other objects and advantages of the present invention will be apparent from the description set forth hereinbelow.

DESCRIPTION OF THE PREFERRED EMBODIMENT

Figure 1:
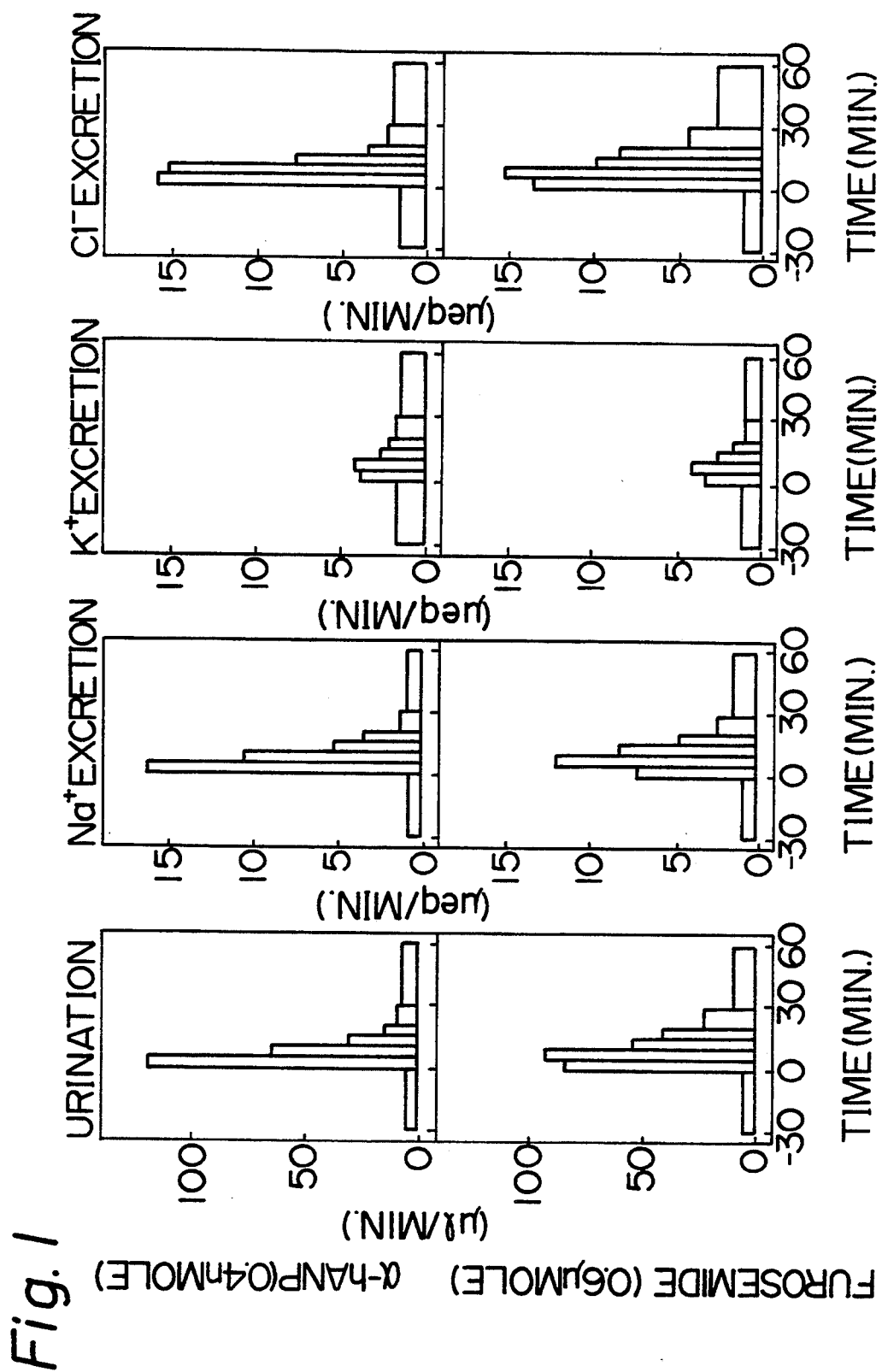
FIG. 1 contains graphs comparing the diuretic action of the α-hANP and furosemide.

At present, furosemide as a natriuretic agent is used for the treatment of essential hypertension. However, the structure of the furosemide is different from that of the new peptide according to the present invention.

The present inventors isolated a peptide, in substantially pure form, consisting of 28 amino acid residues and having a molecular weight of about 3,100, determined the structure of the peptide and found that the peptide showed a notable natriuretic and hypotensive actions.

Structure and Physico-Chemical Properties of the α-hANP

1) Structure

The α-hANP has the structure:

$$\begin{array}{c}
\phantom{xxxxxxxxxxxx}5\phantom{xxxxxxxxxx}10\\
\text{H—Ser—Leu—Arg—Arg—Ser—Ser—Cys—Phe—Gly—Gly—}\\
\phantom{xxxxxxxxxxxxxxxxxxxxxxxxxxx}\text{—Arg—Met—}\\
\phantom{xxxxxxxxxxxxxxxxxxxxxxxxxxx}\text{—Asp—Arg—}①\\
\phantom{xxxxxxxxxxxxxxxxxxxxx}\text{S—S}\\
\phantom{xx}15\phantom{xxxxxxxxxx}20\\
②\text{—Ile—Gly—Ala—Gln—Ser—Gly—Leu—Gly—Cys—}\\
\phantom{xxxxxxxxxxxx}25\\
\text{—Asn—Ser—Phe—Arg—Tyr—OH}
\end{array}$$

wherein ① and ② are directly bonded, Asp represents L-aspartic acid, Asn represents L-asparagine, Ala represents L-alanine, Arg represents L-arginine, Ile represents L-isoleucine, Gly represents glycine, Glu represents L-glutamic acid, Gln represents L-glutamine, Cys represents together with —S— ½ L-cystine, Ser represents L-serine, Tyr represents L-tyrosine, Phe represents L-phenylalanine, Met represents L-methionine, and Leu represents L-leucine, and wherein the amino acid chain has an amino-terminal at the left end and carboxy-terminal at the right end.

2) Molecular weight: about 3,100 as determined by gel-filtration (3080.39 as calculated).

3) Specific rotation: $[\alpha]_D^{25} = -80.0°$ (c=0.16, in 0.1N acetic acid)

4) UV spectrum: Max=275 mm.

5) Color reactions: Ehrlich's reaction, negative; Sakaguchi's reaction, positive; Pauly's reaction, positive.

6) Distinction of basic, acidic, or neutral property: basic.

7) Solubility in solvents: soluble in water, partially in methanol, and acetic acid; insoluble in ethyl acetate, butyl acetate, ethyl ether, hexane, petroleum ether, benzene, and chloroform.

Thin layer chromatography on silica gel: Rf=0.41 (n-butanol:acetic acid:pyridine:water=4:1:1:2); Rf=0.34 (n-butanol:acetic acid:pyridine:water=30:6:20:24); Rf=0.08 (n-butanol:acetic acid:ethyl acetate:water=1:1:1:1).

9) Amino acid composition by amino acid analysis:

| Amino acid | Mol. ratio | |
|---|---|---|
| | found | calculated |
| Asp+ Asn | 2.09 | 2 |
| Ala | 1.12 | 1 |
| Arg | 4.92 | 5 |
| Ile | 1.01 | 1 |
| Gly | 4.99 | 5 |

-continued

| Amino acid | Mol. ratio | |
|---|---|---|
| | found | calculated |
| Glu(Gln) | 1.10 | 1 |
| (Cys)₂ | 0.80(*) | 1 |
| Ser | 4.94 | 5 |
| Tyr | 0.99 | 1 |
| Phe | 1.99 | 2 |
| Met | 0.95 | 1 |
| Leu | 2.00 | 2 |

The amino acid content was determined after a sample was hydrolized with 6N hydrochloric acid, except that the value marked (*) was determined after a sample was oxidized with performic acid, and hydrolized with 6N hydrochloric acid, and cysteine was recovered as $Cys-SO_3H$.

| Elementary analysis: $(C_{127}H_{203}N_{45}O_{39}S_3 \cdot 5CH_3COOH \cdot 8H_2O)$ | | | |
|---|---|---|---|
| | C | H | N |
| Calculated | 46.67 | 6.83 | 17.88 |
| Found | 46.74 | 6.41 | 17.75 |

The analysis was carried out after a sample was treated with Dowex I (in acetate form), and recovered as acetate.

11) Formation of salts: the α-hANP is a basic compound as described in item 6), and can form acid addition salts with an inorganic acid such as hydrochloric acid, sulfuric acid, phosphoric acid, or an organic acid such as formic acid, acetic acid, propionic acid, succinic acid, and citric acid.

Physiological Properties of α-hANP

The α-hANP according to the present invention has notable diuretic, natriuretic, and hypotensive or antihypertensive actions.

Test Method

Male rats weighing 300 to 400 grams were anesthetized by intraperitoneal administration of pentobarbital at a dosage of 60 mg/kg, and used for tests of the α-hANP according to the method described in *Life Sciences*, Vol. 28, pp 89–94.

To keep the respiratory tract open, a tracheal cannula (PE-240 Clay-Adams) was inserted into the trachea. An arterial cannula (PE-50) was inserted into a femoral artery for measurement of the blood pressure, and a venous cannula was inserted into a femoral vein for the administration of Ringer's solution. 1.2 ml of Ringer's solution was injected for ten minutes, and subsequently, was constantly infused at a flow rate of 1.2 ml/hour.

A bladder cannula made of silastic tube with an inner diameter of 0.02 inches and an outer diameter of 0.037 inches was inserted into the bladder, and via the cannula, a urine sample was collected into a test tube. The collection of urine was carried out for 30 minutes before administration of the test compound, and every five minutes after the administration.

A predetermined amount of the test compound α-hANP was dissolved in 50 μl of sterilized physiological saline with 5 μg of bacitracin, and the solution was injected into the jugular vein.

The amount of α-hANP administered was 0.1 n mole (group II), 0.2 n mole (group III), or 0.4 n mole (group IV). The control group (group I) was administered 50 μl of physiological saline containing only bacitracin. For comparison, group V received 50 μl of physiological saline containing bacitracin and 1.21μ mole of furosemide, which is a known natriuretic agent.

Groups I to IV each consisted of three animals, and group V consisted of four animals.

Test Results

The results of the test are set forth in the following table.

| | Control I | α-hANP 0.1 n mole II | α-hANP 0.2 n mole III | α-hANP 0.4 n mole IV | Furosemide 1.21 μ mole V |
|---|---|---|---|---|---|
| Urine volume B[3] (μl/min) A[4] | 5.8 ± 0.3<br>10.9 ± 2.2 | 5.6 ± 1.3<br>21.4 ± 2.4 | 3.9 ± 0.6<br>41.1 ± 7.4 | 6.7 ± 0.9<br>124 ± 13 | 8.6 ± 1.9<br>167 ± 28 |
| Na Excretion (n eq/min) | 618 ± 111<br>1020 ± 166 | 737 ± 362<br>2887 ± 299 | 402 ± 114<br>6031 ± 1282 | 650 ± 93<br>17957 ± 2957 | 1134 ± 283<br>20018 ± 2990 |
| K Excretion (n eq/min) | 2213 ± 348<br>3661 ± 670 | 1944 ± 469<br>6123 ± 1660 | 1687 ± 655<br>6245 ± 818 | 2190 ± 260<br>8992 ± 4218 | 1945 ± 465<br>6897 ± 392 |
| Cl Excretion (n eq/min) | 539 ± 65<br>1247 ± 434 | 1335 ± 452<br>4968 ± 344 | 711 ± 225<br>10155 ± 1962 | 1834 ± 439<br>31972 ± 10032 | 1708 ± 344<br>40242 ± 6859 |
| Na/K ratio | 0.28<br>0.28 | 0.38<br>0.47 | 0.24<br>0.97 | 0.30<br>2.00 | 0.58<br>2.90 |
| Number of animals | 3 | 3 | 3 | 3 | 4 |

[1]All animals received 5 μg bacitracin.
[2]Values are average for 3 or 4 animals.
[3]B is value for sample collected 30 minutes before administration of test compound.
[4]A is value for sample collected 5 minutes after administration of test compound.

As shown in the table, α-hANP shows notable diuretic and natriuretic actions. Namely, 0.4 n mole of α-hANP injected into the jugular vein of a rat provides diuretic and natriuretic action comparable to those provided by 1.21μ mole of furosemide, which is a known diuretic agent. 0.4 n mole of α-hANP gives about a 20-fold increase in the urination volume, and about a 27-fold increase in the sodium excretion. When α-hANP is not administrated, the Na/K ratio in urine is about 0.3, but when 0.4 n mole of α-hANP is administrated, this ratio rises to about 2.0, revealing that α-hANP is useful as a natriuretic agent.

Figure 2:
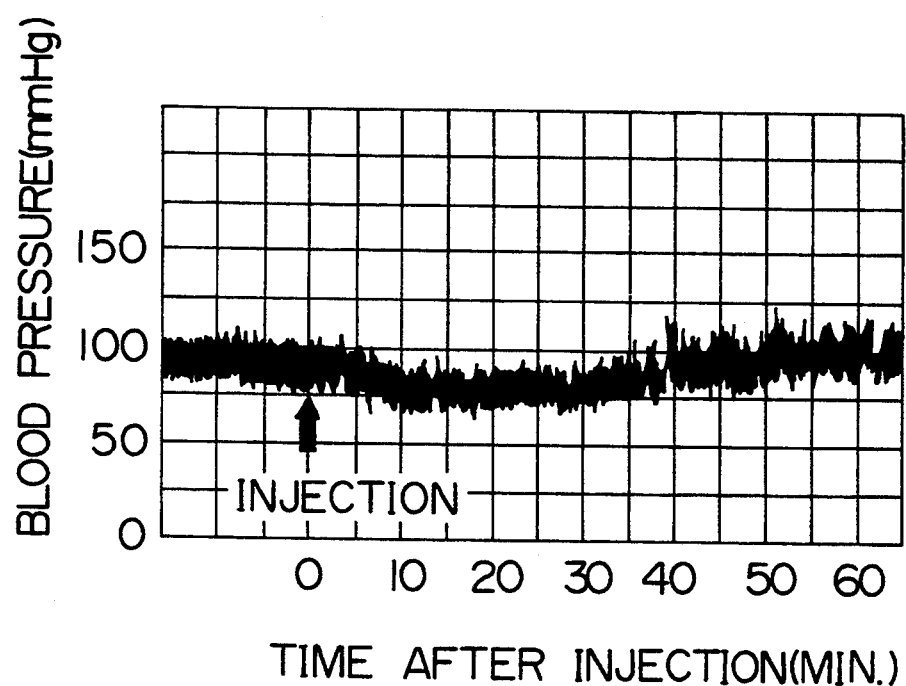
FIG. 2 is a chart showing the hypotensive action of the α-hANP.

FIG. 1 shows comparisons between α-hANP and furosemide regarding changes in the urination volume, and the excretions of sodium cation, potassium cation, and chlorine anion after the administration of α-hANP or furosemide. As shown in the Figure, α-hANP causes diuretic and natriuretic actions more rapidly than furosemide. As shown in FIG. 2, after 1.2 μg (0.4 n mole) of α-hANP is administered to a rat, the blood pressure is lowered by about 15 to 20 mmHg for about 45 minutes, revealing that α-hANP has a hypotensive action or antihypertensive action, and may be useful as a hypotensor.

Use of α-hANP as a pharmaceutical product

Repeated administration of α-hANP does not stimulate production of antibodies, and does not cause anaphylaxis shock. α-hANP consisting of L-amino acids is gradually hydrolized in a body providing the L-amino acids, and therefore shows little toxicity.

Due to the higher diuretic, natriuretic, and blood pressure-lowering or antihypertensive actions, and the lower toxicity, α-hANP is useful as an active ingredient for pharmaceutical compositions such as a diuretic and a hypotensor. α-hANP is administered at 1 ng/kg to 10 mg/kg, preferably 10 ng/kg to 1 mg/kg.

α-hANP can be administered in the same manner as conventional peptide type pharmaceuticals. Namely, α-hANP is preferably administered parenterally, for example, intravenously, intramuscularly, intraperitoneally, or subcutaneously. α-hANP, when administered orally, may be proteolytically hydrolyzed. Therefore, oral application is not usually effective. However, α-hANP can be administered orally as a formulation wherein α-hANP is not easily hydrolyzed in a digestive tract, such as liposome-microcapsules. α-hANP may be also administered in suppositories, sublingual tablets, or intranasal spray.

The parenterally administered pharmaceutical composition is an aqueous solution containing about 0.000005 to 5%, preferably 0.00005 to 0.5% of α-hANP, which may contain, in addition to α-hANP as an active ingredient, for example, buffers such as phosphate, acetate, etc., osmotic pressure-adjusting agents such as sodium chloride, sucrose, and sorbitol, etc., antioxidative or antioxygenic agents, such as ascorbic acid or tocopherol and preservatives, such as antibiotics. The parenterally administered composition also may be a solution readily usable or in a lyophilized form which is dissolved in sterile water before administration.

Production of α-hANP

α-hANP can be produced by either the extraction of the α-hANP from human atrium or by chemical synthesis.

In the former process, human atrium is homogenized in an acidic aqueous solution such as a phosphate buffer solution, or an acetic acid solution containing hydrochloric acid. Subsequently, α-hANP is purified according to a conventional method suitable for the purification of peptide, such as centrifugation, isoelectric point precipitation, solvent extraction, ultrafiltration, gel filtration, adsorption chromatography or high performance liquid chromatography (HPLC), or a combination of such methods. In the above-mentioned methods, chicken rectum relaxation activity is conveniently used to select fractions containing α-hANP, because α-hANP has this activity. In the chromatography methods, the α-hANP containing fractions can be also selected by molecular weight (about 31000). Chemical synthesis is preferable for the industrial production of α-hANP, in which chemical synthesis, a liquid phase method or solid phase method, or a combination thereof can be used. The solid phase method such as Merrifield's method [R. B. Merrifield, J. Am. Chem. Soc. 85, 2148 (1963)] is most convenient.

In Merrifield's method, each amino acid is protected preferably with tert-butyloxycarbonyl (Boc) at the α-amino group; a hydroxyl group in tyrosine is protected preferably with 2,6-dichlorobenzyl group ($Cl_2Bzl$); a guanidino group in arginine is protected preferably with a tosyl group (Tos); a hydroxyl group in serine is protected preferably with a benzyl group (Bzl); a β-carboxyl group in aspartic acid is protected preferably with an O-benzyl group (O-Bzl); and a thiol group in cysteine is protected preferably with an acetoamidomethyl group (Acm). In the Merrifield method, first a protected derivative of C-terminal amino acid L-tyrosin, i.e., Boc-Tyr ($Cl_2Bzl$) is introduced onto a solid phase resin carrier, such as chloromethyl-resin, and subsequently, each suitably protected amino acid is coupled to a terminal amino acid of an intermediate amino acid chain bonded to the resin, in the order of the amino acid sequence of α-hANP. After all the amino acids are coupled in the predetermined order, the protected α-hANP thus obtained is removed from the resin by treatment with hydrogen fluoride, and simultaneously, protecting groups other than Acm are also removed. The product is then reduced to obtain Cys $^{7,23}$(Acm)-α-hANP), which is then oxidized with iodine to remove the thiol-protecting group Acm, and simultaneously, to form a disulfide bond. The crude α-hANP thus obtained is then purified by conventional methods such as gel filtration, reverse phase HPLC, etc., to obtain purified α-hANP.

EXAMPLES

The present invention will now be further illustrated by, but is by no means limited to, the following examples.

Example 1 Preparation of α-hANP from Human Atrium Cordis

Ten hours after death, 40 g of human atrium cordis was removed and boiled in seven volumes of 1M acetic acid aqueous solution containing 20 mM hydrochloric acid for five minutes, to inactivate protease present in the atrium cordis. The boiled atrium cordis in the acetic acid solution was then cooled to 4° C., and homogenized with a Polytron homogenizer to extract the α-hANP. The homogenate thus obtained was centrifuged at 12000 XG for 30 minutes to obtain a supernatant. To the supernatant, acetone was dropwise added in an amount of 66% of the final concentration to precipitate impurities. The mixture thus obtained was centrifuged to obtain 424 ml of supernatant containing α-hANP, which was then evaporated to dryness. The residue thus obtained was dissolved in 1N acetic acid, and the solution was extracted two times with 50 ml of ethyl ether to defat the solution. The aqueous phase thus obtained was lyophilyzed, and the lyophilyzate was redissolved in 100 ml of 1N acetic acid. The solution was then ultrafiltrated with a UM-2 filter (Amicon) to desalt the solution. The desalted solution was concentrated to 50 ml.

The concentrated solution was applied on SP-Sephadex C-25 column (Pharmacia, 8.0×22 cm). The elution was carried out with 1N acetic acid, 2N pyridine solution, and 2N pyridine-1N acetic acid solution (pH 5.0), in that order, to obtain fractions SP-I, SP-II, and SP-III. The fraction SP-III was lyophylized to obtain 26.6 mg of lyophylizate, which was then dissolved in 1N acetic acid.

Figure 3:
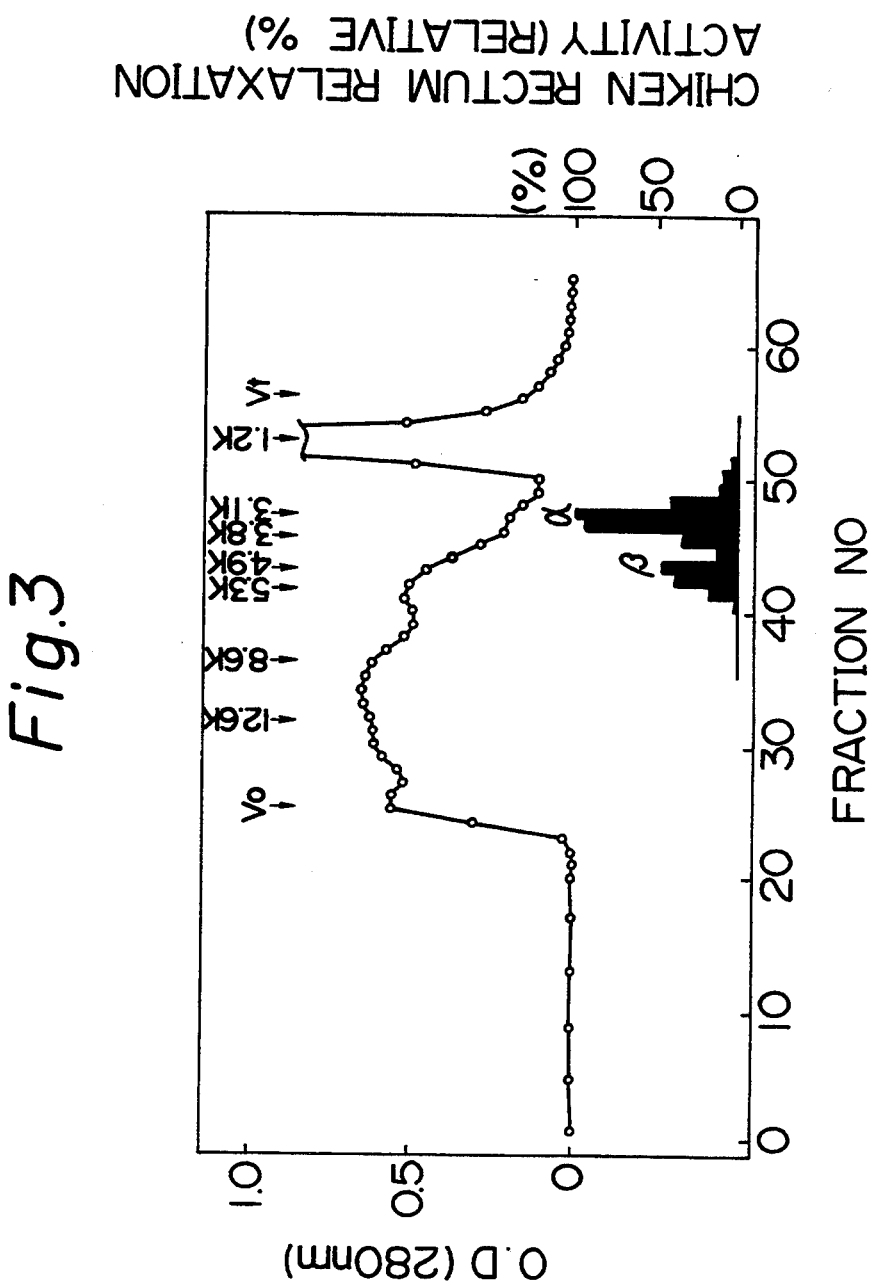
FIG. 3 is a chromatogram showing an elution profile wherein the α-component is separated from the β-component by gel filtration with Sephadex G-50 during isolation of the α-hANP from human atrium.

The solution thus obtained was gel-filtrated with Sephadex G-50 column (1.2×103 cm) at a flow rate of 5.4 ml/hour, collecting 2 ml of fractions. Thereby, β fractions (fractions No. 42 to 45) and a fractions (fractions No. 46 to 51) which have chicken rectum relaxation activity were obtained. The elution profile is shown in FIG. 3. The α fractions were combined for further purification.

The combined fraction was then subjected to cation exchange HPLC in a TSK-CM3SW column (Toyo Soda). Elution was carried out by linear gradient with (A) 10 mM ammonium formate (pH 6.6)/acetonitrile (90:10) and (B) 1.0M ammonium formate (pH 6.6)/acetonitrile (90:10), changing the concentration of formate from 10 mM to 0.5M for 80 minutes. A set of fractions (No. 57 to 59) with chicken rectum relaxation activity was obtained. The active fractions were combined and subjected to reverse phase HPLC in a Chemcosorb 5 ODS H column ($\phi$4.6×250 mm, Chemco). Elution was carried out with (A) water/acetonitrile/10% trifluoroacetic acid (90:10:1) and (B) water/acetonitrile/10% trifluoroacetic acid (40:60:1) as eluents wherein the eluent (A) was used for 8 minutes and then linear gradient from (A) to (B) was used for 80 minutes, at a flow rate of 1.0 ml/min., and pressure of 110 to 130 kg/cm². A main peak was collected and 30 μg of substantially pure α-hANP was obtained.

Example 2 Chemical Synthesis of α-hANP (1) Synthesis of aminoacyl resin

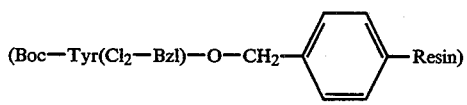

To 3 g of chloromethyl resin with 0.92 m mole/g resin of chloro radical in 15 ml of dimethylformamide, 10 ml of solution of Boc-Tyr(Cl₂Bzl)-OH cesium salt in dimethylformamide was added with stirring. The cesium salt was prepared from 1.22 g (2.76 m mole) of Boc-Tyr(Cl₂Bzl)-OH and 0.90 g (2.76 m mole) of cesium carbonate. The mixture thus obtained was gently stirred at 50° C. for 12 hours. The resin was filtered off, and washed with dimethylformamide, ethanol, water, ethanol, and methylene chloride in that order, and dried. The washed resin was then stirred with an excess amount of cesium acetate in dimethylformamide at 50° C. for 24 hours to acetylate residual chloro radical which had not reacted with Boc-Tyr(Cl₂Bzl)-OH, and then washed as described above. 3 g of

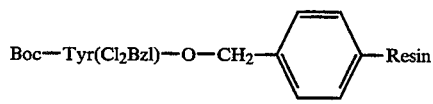

containing 0.7 m mole/g resin of Boc-Tyr(Cl₂Bzl)-OH was obtained. The introduction rate was determined by the HF method and the HCl-propionic acid hydrolysis method.

(2) Synthesis of protected α-hANP-Resin

Each amino acid was protected with a Boc group at an α-amino group. A hydroxyl group in tyrosine was protected with a Cl₂Bzl group; a guanidino group in arginine was protected with a Tos group; a hydroxyl group in serine was protected with a Bzl group; a β-carboxyl group in aspartic acid was protected with an OBzl group; and a thiol group in cysteine was protected with an Acm group. Among these protecting groups, the Boc group is easily removed with 50% trifluoroacetic acid. Protecting groups other than the Boc group and Acm group are not removed with 50% trifluoroacetic acid, but removed with hydrogen fluoride. The Acm group is not removed with 50% fluoroacetic acid and hydrogen fluoride, but removed by oxidation with iodine, and simultaneously, a disulfide bond is formed.

Prior to coupling of an amino acid, a protecting group for the α-amino group of the terminal amino acid of the protected intermediate peptide bonded to the resin, i.e., the Boc group, has been removed to free the terminal α-amino group. The progression and completion of the Boc removing reaction were monitered with Kaiser's reagent (ninhydrin reagent).

After the protecting group was removed from the terminal α-amino group of the protected peptide bonded to the resin, the resulting free amino group was coupled with a free carboxyl group of a Boc-protected derivative of an amino acid positioned at the next position in the amino acid sequence of the α-hANP.

In the coupling reaction of the protected amino acid, the coupling reaction of the Boc-Asn-OH was carried out using 10 equivalents of Boc-Asn-OH for 40 hours according to the p-nitrophenol ester method. The coupling reaction of other protected amino acids was carried out using 6 equivalents of the protected amino acid and 6 equivalents of dicyclohexylcarbodiimide as a condensation reagent. If the coupling reaction was not complete after one operation of the above-mentioned procedure, the same procedure was repeated. If the coupling reaction was not complete after the procedure was repeated three times, the resin was treated with a solution of 10% acetic anhydride/pyridine (9:1) in methylene chloride to acetylate any unreacted amino group. Subsequently, the next coupling reaction was carried out. The progression and completion of the coupling reaction was monitored with Kaiser's reagent (ninhydrin reagent) as described above for the Boc group removing reaction.

by repeating the above-described procedure, starting with 3 g of

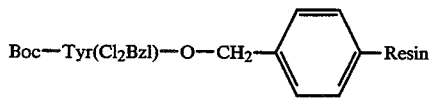

(0.70 m mole/g resin), 6.6 g of

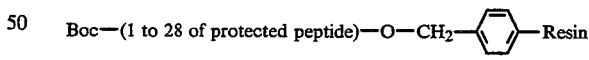

was obtained.

(3) Cut off from resin, deprotection and purification of peptide, and formation of disulfide bond 3 g of the protected peptide-Resin was wetted with 5 ml of anisole, treated with hydrogen fluoride at 0° C. for 60 minutes, and an excess amount of the hydrogen fluoride was evaporated off. By the above-mentioned treatment, the protected peptide was cut off from the resin, and protecting groups other than the thiol protecting Acm group were removed. 200 ml of 1N acetic acid was added to the mixture, and the mixture was stirred for 30 minutes and filtrated to remove the resin.

The filtrate was then washed with ethyl ether, adjusted to pH 8.0 with 5% ammonium hydroxide, and reduced by incubation with 2.3 g of dithiothreitol at 37° C. for 24 hours. The reduction reduced most of the Met (O) derivative, as confirmed with reverse HPLC. Moreover, O-peptide, which could be formed when a peptide containing Ser or Thr is treated with hydrogen fluoride, was reduced to a normal peptide.

The reaction mixture (about 300 ml) thus treated was then adsorbed to an Octa-Deca-Silica (ODS) column ($\phi$4 cm×5 cm, Waters), the column was washed with water, and peptide was eluted with 60% acetonitrile to obtain 850 mg of inorganic-salts-free peptide. 650 mg of the peptide was purified by ion exchange chromatography with CM-Sepharose, wherein the peptide sample was applied to a CM-Sepharose column ($\phi$1.5 cm×45 cm) equilibrated with 50 mM ammonium acetate (pH 4.0), and eluted by linear gradient from 500 ml of 50 mM ammonium acetate (pH 4.0) to 500 ml of 0.5M ammonium acetate (pH 7.0), to obtain a main peak. The eluate was passed through an ODS column ($\phi$4 cm×5 cm), to desalt the eluate, and lyophilized to obtain 127 mg (dry weight) of roughly pure peptide $^{7,23}$Cys(Acm)-α-hANP.

50 mg (dry weight) of the $^{7,23}$Cys(Acm)-α-hANP in 60 ml of acetic acid and 1.6 ml of water was then added all at once to a solution of 170 mg of iodine in 40 ml of acetic acid, 18 ml of water and 80 μl of 1N hydrochloric acid, and the mixture was vigorously stirred. After ten minutes, L-ascorbic acid buffer solution was added to the mixture until the reaction mixture became clear. The mixture was then diluted with water to ten volumes, passed through an ODS column ($\phi$4 cm×5 cm) to desalt the mixture, and lyophylized to obtain 30.2 mg (dry weight) of a lyophylizate comprising α-hANP, $^{7,23}$Csy(Acm)-α-hANP, and Met(O)-$^{7,23}$Cys(Acm)-α-hANP, at a ratio of 3:1:1.

Figure 4:
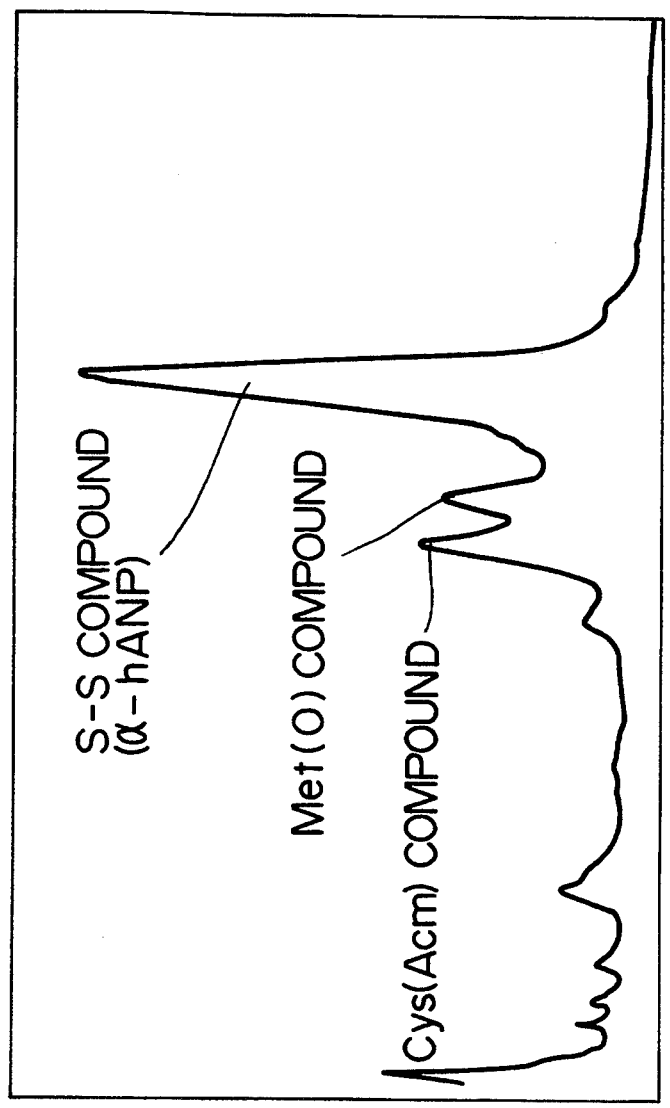
FIG. 4 is a chart showing a separation profile wherein α-hANP (S—S compound) is separated from a by-product Cys (Acm) compound and Met (O) compound at the last stage of chemical synthesis.

17.3 mg of the lyophilizate was separated into the above-mentioned three components by cation exchange HPLC using a TSK-CM2SW column (Toyo Soda), and 4.5 mg of α-hANP was obtained having a purity of about 95%. A profile of the HPLC is shown in FIG. 4.

Example 3 Preparation of Parenteral Composition

A) Injection solution

| A) Injection solution Composition | |
|---|---|
| α-hANP | 2 g |
| sodium chloride | 8 g |
| ascorbic acid | 2 g |
| sterile water | 1 l |

Method

α-hANP and sodium chloride were dissolved in sterile water, an ampule was filled with 5 ml of the solution, and the ampule was then sealed.

B) Lyophilizate

| B) Lyophilizate Composition | |
|---|---|
| α-hANP | 2 g |
| sorbitol | 20 g |

Method

α-hANP and sorbitol were dissolved in 200 ml of sterile water, a vial was filled with 1 ml of the solution, and lyophilized, and the vial was then sealed.

The composition is dissolved in 5 ml of sterile water before parenteral administration.

We claim:

1. A peptide α-hANP having the following formula:

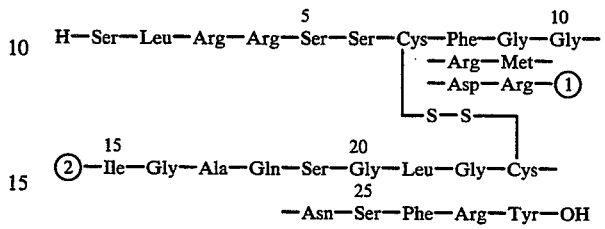

wherein ① and ② are directly bonded, Asp represents L-aspartic acid, Asn represents L-asparagine, Ala represents L-alanine, Arg represents L-arginine, Ile represents L-isoleucine, Gly represents glycine, Glu represents L-glutamic acid, Gln represents L-glutamine, Cys represents together with —S— ½ L-cysteine, Ser represents L-serine, Tyr represents L-Tyrosine, Phe represents L-phenylalanine, Met represents L-methionine, and Leu represents L-leucine, and the amino acid chain has an amino-termical at the left end, and carboxy-terminal at the right end, and acid addition salts thereof.

2. A pharmaceutical composition for use as a diuretic or antihypertensive agent comprising a diuretically effective amount or an antihypertensively effective amount of a peptide α-hANP having the following formula:

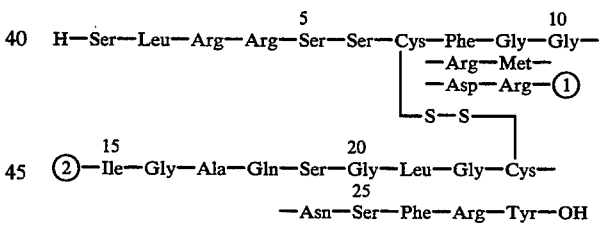

or an acid addition salt thereof with a conventional pharmaceutical additive.

3. The pharmaceutical composition according to claim 2, wherein the composition is a solution for parenteral administration and the conventional pharmaceutical additive is a buffer, an osmotic pressure adjusting agent or a preservative, or a combination thereof.

4. The pharmaceutical composition according to claim 2, wherein the composition is a solution for parenteral administration and contains about 0.000005 to 5% of the α-hANP.

5. The pharmaceutical composition according to claim 2, wherein the composition is in a lyophylized form.

6. A method for promoting diuresis comprising administering a diuretically effective amount of a peptide α-hANP having the following formula:

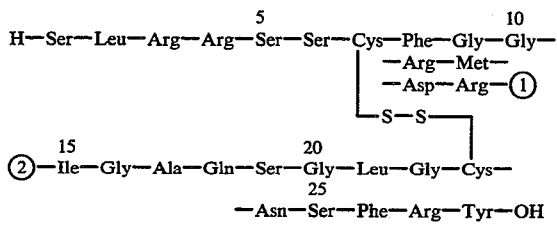

or an acid addition salt thereof with a conventional pharmaceutical additive.

7. The method according to claim 6, wherein the conventional pharmaceutical additive is a buffer, an osmotic pressure adjusting agent or a preservative, or a combination thereof.

8. The method according to claim 6, wherein about 0.000005 to 5% of the α-hANP based on the weight of the α-hANP and additive is administered parenterally.

9. A method for lowering blood pressure comprising administering an antihypertensively effective amount of a peptide α-hANP having the following formula:

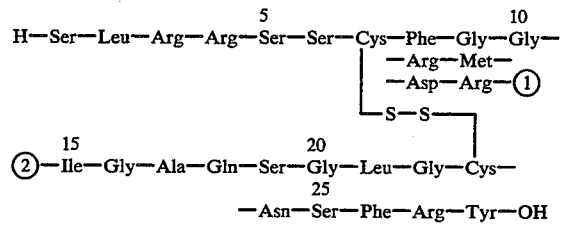

or an acid addition salt thereof with a conventional pharmaceutical additive.

10. The method according to claim 9, wherein the conventional pharmaceutical additive is a buffer, an osmotic pressure adjusting agent or a preservative, or a combination thereof.

11. The method according to claim 9, wherein about 0.000005 to 5% of the α-hANP based on the weight of the α-hANP and additive is administered parenterally.

12. A peptide α-hANP in isolated form having the following formula:

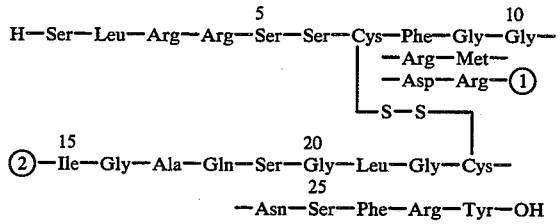

wherein ①  and ②  are directly bonded, Asp represents L-aspartic acid, Asn represents L-asparagine, Ala represents L-alanine, Arg represents L-arginine, Ile represents L-isoleucine, Gly represents glycine, Glu represents L-glutamic acid, Gln represents L-glutamine, Cys represents together with —S— ½ L-cystine, Ser represents L-serine, Tyr represents L-tyrosine, Phe represents L-phenylalanine, Met represents L-methionine, and Leu represents L-leucine, and the amino acid chain has an amino-terminal at the left end, and carboxy-terminal at the right end, and acid addition salts thereof.

* * * * *